United States Patent
Tiefenbruck et al.

(10) Patent No.: US 9,102,690 B2
(45) Date of Patent: Aug. 11, 2015

(54) ACICULAR BOEHMITE NANOPARTICLES

(75) Inventors: Grant F. Tiefenbruck, Cottage Grove, MN (US); Brant U. Kolb, Afton, MN (US); Thomas E. Wood, Stillwater, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 643 days.

(21) Appl. No.: 12/810,041

(22) PCT Filed: Dec. 17, 2008

(86) PCT No.: PCT/US2008/087077
§ 371 (c)(1),
(2), (4) Date: Jun. 22, 2010

(87) PCT Pub. No.: WO2009/110945
PCT Pub. Date: Nov. 9, 2009

(65) Prior Publication Data
US 2010/0267881 A1    Oct. 21, 2010

(51) Int. Cl.
*C08K 3/18* (2006.01)
*C01F 7/00* (2006.01)
*C07F 5/06* (2006.01)

(52) U.S. Cl.
CPC ........... *C07F 5/069* (2013.01); *Y10T 428/2991* (2015.01)

(58) Field of Classification Search
CPC ............... C01F 7/02; C01F 7/04; C01F 7/34; C01F 7/36; C07F 5/069
USPC ............................ 423/625, 626, 111; 977/773
See application file for complete search history.

(56) References Cited

U.S. PATENT DOCUMENTS

| | | | |
|---|---|---|---|
| 2,915,475 A | 12/1959 | Bugosh | |
| 3,031,418 A | 4/1962 | Bugosh | |
| 3,601,378 A | 8/1971 | Hurst | |
| 3,941,719 A | 3/1976 | Yoldas | |
| 3,957,598 A * | 5/1976 | Merkl | 528/271 |
| 4,798,814 A | 1/1989 | Everitt | |
| 5,055,019 A | 10/1991 | Meyer | |
| 5,453,262 A | 9/1995 | Dawson | |
| 5,480,630 A * | 1/1996 | Arai et al. | 423/625 |
| 5,652,192 A | 7/1997 | Matson | |
| 6,264,710 B1 | 7/2001 | Erickson | |
| 6,277,161 B1 * | 8/2001 | Castro et al. | 51/309 |
| 6,369,183 B1 * | 4/2002 | Cook et al. | 528/10 |

(Continued)

FOREIGN PATENT DOCUMENTS

| | | |
|---|---|---|
| EP | 1630135 | 3/2006 |
| WO | WO 2005/100244 | 10/2005 |

OTHER PUBLICATIONS

Byrappa (Hydrothermal technology for nanotechnology, Progress in Crystal growth and Characterization of Materials, 2007, 53:117-166).*

Adschiri, "Rapid and Continuous Hydrothermal Crystallization of Metal Oxide Particles in Supercritical Water", Journal of American Ceramic Society, Apr. 1992, vol. 75, No. 4, pp. 1019-1022.

(Continued)

*Primary Examiner* — Jun Li
(74) *Attorney, Agent, or Firm* — Jean A. Lown

(57) ABSTRACT

Acicular boehmite nanoparticles, methods of making acicular boehmite nanoparticles, and composite materials that contain acicular boehmite nanoparticles are described. The acicular boehmite nanoparticles are prepared in a continuous hydrothermal reactor from a feedstock solution containing a soluble aluminum-containing precursor.

15 Claims, 2 Drawing Sheets

(56) References Cited

U.S. PATENT DOCUMENTS

| | | |
|---|---|---|
| 7,189,775 B2 | 3/2007 | Tang |
| 2004/0265219 A1 | 12/2004 | Bauer |
| 2007/0098990 A1* | 5/2007 | Cook et al. .................. 428/404 |
| 2008/0015299 A1* | 1/2008 | Takemura et al. ............ 524/437 |

OTHER PUBLICATIONS

Adschiri, "Rapid and Continuous Hydrothermal Synthesis of Boehmite Particles in Subcritical and Supercritical Water", Journal of American Ceramic Society, Sep. 1992, vol. 75, No. 9, pp. 2615-2618.

International Search Report for PCT/US2008/087077, 3 pgs.

* cited by examiner

ACICULAR BOEHMITE NANOPARTICLES

CROSS REFERENCE TO RELATED APPLICATIONS

This application is a national stage filing under 35 U.S.C. 371 of PCT/US2008/087077, filed Dec. 17, 2008, which claims priority to Provisional Application No. 61/017,267, filed Dec. 28, 2007, the disclosure of which is incorporated by reference in its/their entirety herein.

TECHNICAL FIELD

This invention relates to acicular boehmite nanoparticles, methods of making acicular boehmite nanoparticles, and composite materials that contain acicular boehmite nanoparticles.

BACKGROUND

Methods of making boehmite are known. Many of these methods, however, do not produce boehmite that is acicular or that is in the nanoparticle size range. Some methods that are known for preparing acicular boehmite require excessively long heating times such as several hours to several days.

SUMMARY

The present invention provides acicular boehmite nanoparticles and methods of making acicular boehmite nanoparticles. The acicular boehmite nanoparticles have an average length that is no greater than 1000 nanometers. The nanoparticles are usually crystalline and substantially non-associated. The acicular boehmite nanoparticles can be added to an organic matrix material for a variety of purposes such as, for example, improving the tensile strength of a polymeric material or thickening an organic matrix.

In one aspect, a method of making an acicular boehmite nanoparticle is provided. The method includes providing a feedstock solution that includes an aluminum-containing precursor dissolved in an aqueous-based solvent at a pH no greater than 6. The aluminum-containing precursor is of Formula (I).

$$Al(OH)_w(R^1)_x(R^2)_y(R^3)_z \quad (I)$$

In Formula (I), $R^1$ is a first carboxylate selected from formate or acetate. Group $R^2$ is a second carboxylate that is different than the first carboxylate and that is selected from acetate, propionate, butyrate, or mixtures thereof. Group $R^3$ is an optional third mono-carboxylate having at least 5 carbon atoms. The sum of the variables w, x, y, and z is equal to 3 with w being in the range of 1.5 to 2.2, x being at least 0.1, y being at least 0.1, and z being in the range of 0 to 0.2. The method further includes passing the feedstock solution through a continuous hydrothermal reactor. An effluent of the continuous hydrothermal reactor contains the acicular boehmite nanoparticle.

In another aspect, an acicular boehmite nanoparticle is provided. Various sorbed modifiers are on a surface of the acicular boehmite nanoparticle. The sorbed modifiers include (a) a first carboxylic acid, an anion of the first carboxylic acid, or a mixture thereof and (b) a second carboxylic acid, an anion of the second carboxylic acid, or a mixture thereof. The first carboxylic acid is selected from formic acid or acetic acid. The second carboxylic acid, which is different than the first carboxylic acid, is selected from acetic acid, formic acid, propionic acid, butyric acid, or a mixture thereof.

In yet another aspect, a composite material is provided that includes an organic matrix and an acicular boehmite nanoparticle dispersed or suspended in the organic matrix. Various sorbed modifiers are on a surface of the acicular boehmite nanoparticle. The sorbed modifiers include (a) a first carboxylic acid, an anion of the first carboxylic acid, or a mixture thereof and (b) a second carboxylic acid, an anion of the second carboxylic acid, or a mixture thereof. The first carboxylic acid is selected from formic acid or acetic acid. The second carboxylic acid, which is different than the first carboxylic acid, is selected from acetic acid, formic acid, propionic acid, butyric acid, or a mixture thereof.

The above summary of the present invention is not intended to describe each disclosed embodiment or every implementation of the present invention. The Figure, Detailed Description and Examples that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
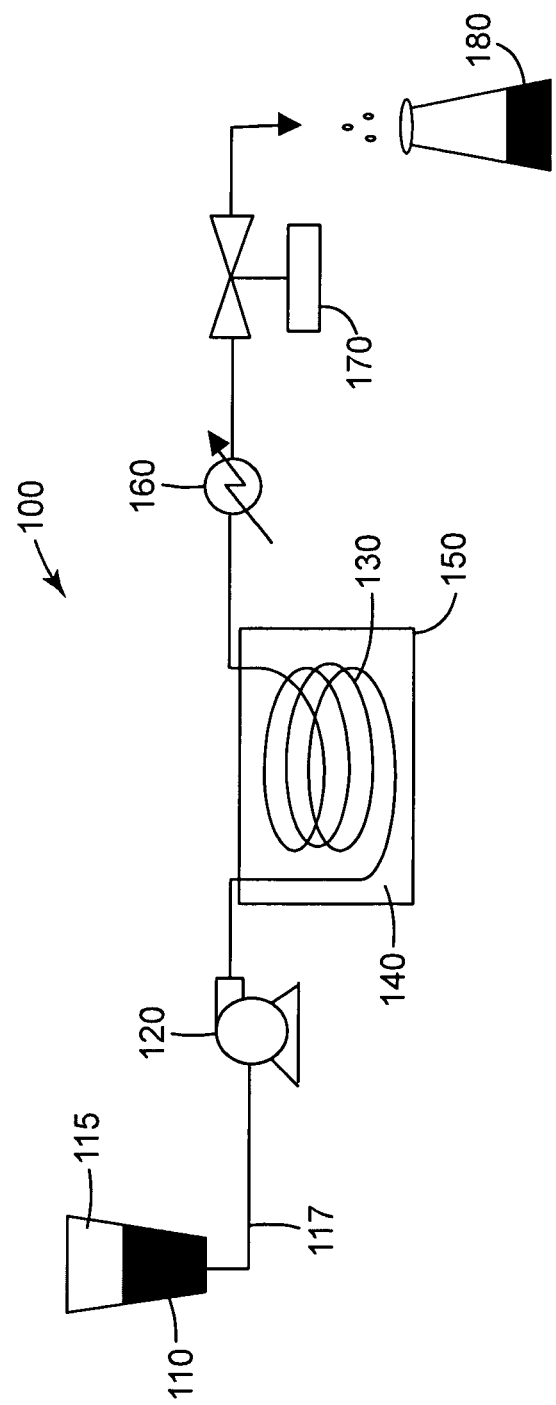
FIG. 1 schematically illustrates an exemplary continuous hydrothermal reactor system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Acicular boehmite nanoparticles, methods of making acicular boehmite nanoparticles, and composite materials that contain acicular boehmite nanoparticles are described. The acicular boehmite nanoparticles, which are prepared in a continuous hydrothermal reactor, typically have an average length no greater than 1000 nanometers and an average aspect ratio equal to at least 3:1.

As used herein, the term "organic matrix" refers to a polymeric material or a precursor (e.g., monomer or oligomer) to a polymeric material. That is, the organic matrix can contain polymerized material, polymerizable material, or a mixture thereof.

In one aspect, a method of making an acicular boehmite nanoparticle is provided. The method includes providing a feedstock solution containing an aluminum-containing precursor dissolved in an aqueous-based solvent at a pH no greater than 6. The feedstock solution is passed through a continuous hydrothermal reactor. The aluminum-containing precursor undergoes hydrolysis and condensation reactions within the continuous hydrothermal reactor that result in the formation of the acicular boehmite nanoparticle.

As used herein, the term "continuous hydrothermal" refers to a method of heating an aqueous medium at a temperature above the normal boiling point of the aqueous medium at a pressure that is equal to or greater than the pressure required to prevent boiling of the aqueous medium. A feedstock is continually introduced into a heated zone and an effluent is continually removed from the heated zone of the continuous hydrothermal rector. The continual introduction of the feedstock and continual removal of the effluent can be constant or intermittent (e.g., pulsed). The introduction of the feedstock and the removal of the effluent typically occur in different regions of the heated zone.

As used herein, the term "boehmite" refers to a material that is predominantly gamma-aluminum oxy hydroxide (γ-AlOOH).

The aluminum-containing precursor that is dissolved in the feedstock solution for the continuous hydrothermal continuous reactor is of Formula (I).

In Formula (I), $R^1$ is a first carboxylate selected from formate or acetate. Group $R^2$ is a second carboxylate that is different than the first carboxylate and that is selected from acetate, propionate, butyrate, or a mixture thereof. Group $R^3$ is an optional third mono-carboxylate having at least 5 carbon atoms. The sum of the variables w, x, y, and z is equal to 3 with w being in the range of 1.5 to 2.2, x being at least 0.1, y being at least 0.1, and z being in the range of 0 to 0.2.

The aluminum-containing precursor of Formula (I) can be prepared by any known process. In many embodiments, this aluminum-containing precursor is prepared by digesting aluminum metal in a mixture of water and at least two different carboxylic acids. At least two of the carboxylic acids are mono-carboxylic acids (i.e., the carboxylic acids each have a single carboxyl group) having 1 to 4 carbon atoms. A first carboxylic acid is usually formic acid or acetic acid. A second carboxylic acid, which is different than the first carboxylic acid, is usually acetic acid, propionic acid, butyric acid, or a mixture thereof. An optional third mono-carboxylic acid can contain at least 5 carbon atoms. In some embodiments, the first carboxylic acid is formic acid, the second carboxylic acid is acetic acid, propionic acid, butyric acid, or a mixture thereof, and there is no third carboxylic acid having at least 5 carbon atoms.

The optional third carboxylic acid having at least 5 carbon atoms is often a mono-carboxylic acid having a poly(alkylene oxide) group. The third carboxylic acid often has up to 30 carbon atoms, up to 20 carbon atoms, up to 18 carbon atoms, up to 16 carbon atoms, up to 14 carbon atoms, or up to 12 carbon atoms. For example, the third carboxylic acid can be of Formula (II).

In Formula (II), $R^4$ is an alkyl group having 1 to 4 carbon atoms, $R^5$ is an alkylene group having 1 to 4 carbon atoms, and the variable n is an integer in the range of 1 to 10.

For example, the third carboxylic acid can be, but is not limited to, 2-[2-(2-methoxyethoxy)ethoxy]acetic acid (MEEAA) and 2-(2-methoxyethoxy)acetic acid (MEAA).

Stated differently, the optional group $R^3$ in Formula (I) is often a mono-carboxylate having a poly(alkylene oxide) group. Groups $R^3$ often has 5 to 30 carbon atoms, 5 to 20 carbon atoms, 5 to 16 carbon atoms, or 5 to 12 carbon atoms. In some embodiment, $R^3$ is of Formula (III)

where $R^4$ and $R^5$ are the same as defined for Formula (II). Exemplary $R^3$ groups include, but are not limited to, 2-[2-(2-methoxyethoxy)ethoxy]acetate and 2-(2-methoxyethoxy)acetate.

The digestion mixture for preparing the aluminum-containing precursor of Formula (I) is usually heated in the range of 70° C. to 100° C. for at least 1 hour, at least 2 hours, at least 4 hours, at least 6 hours, at least 8 hours, or at least 10 hours.

A reflux condenser is often used to minimize the loss of any of the carboxylic acids or water. The reaction is typically terminated when hydrogen evolution ceases from the digestion mixture and no aluminum metal is visible within the digestion mixture.

The amount of aluminum, first carboxylic acid, second carboxylic acid, and optional third carboxylic acid in the digestion mixture can be selected to produce the desired aluminum-containing precursor of Formula (I). Further, the total concentration of aluminum-containing precursor formed can be varied by altering the concentration of the reactants added to the digestion mixture.

The concentration of aluminum metal added to the digestion mixture is usually greater than 0.1 molar. If lower concentrations are used, the amount of the precursor formed may be unacceptably low and a concentration step may be needed prior to being used as the feedstock solution for the continuous hydrothermal reactor. The concentration of aluminum metal is often at least 0.2 molar, at least 0.5 molar, at least 0.75 molar, at least 1.0 molar, at least 1.25 molar, at least 1.5 molar, at least 1.75 molar, or at least 2.0 molar. The aluminum metal concentration in the digestion mixture can be up to 5 molar or greater. If the concentration is too high, however, the viscosity of the digestion mixture may be unacceptably high for good mixing. The aluminum metal concentration often can be up to 4 molar, up to 3 molar, or up to 2 molar. In some digestion mixtures, the aluminum metal concentration is in the range of 0.1 to 5 molar, in the range of 0.5 to 5 molar, in the range of 0.5 to 4 molar, in the range of 0.5 to 3 molar, or in the range of 0.5 to 2 molar.

For every mole of aluminum metal added to the digestion mixture, the total amount of carboxylic acid is typically in the range of 0.8 to 1.5 moles. That is, for every mole of aluminum added, there is often a total of 0.8 to 1.5 moles of the first carboxylic acid plus the second carboxylic acid plus the optional third carboxylic acid. In some examples, the total amount of carboxylic acid is in the range of 0.9 to 1.5 moles, in the range of 1.0 to 1.5 moles, or in the range of 1.0 to 1.4 moles per mole of aluminum.

For every mole of aluminum metal added to the digestion metal, at least 0.1 moles of the first carboxylic acid is typically added. In many embodiments, at least 0.2 moles, at least 0.3 moles, at least 0.4 moles, at least 0.5 moles, at least 0.6 moles, at least 0.7 moles, at least 0.8 moles, at least 0.9 moles, or at least 1.0 moles of the first carboxylic acid are added for every mole of aluminum metal present in the digestion mixture. For example, the amount of the first carboxylic acid can be in the range of 0.1 to 1.4 moles, in the range of 0.2 to 1.4 moles, in the range of 0.3 to 1.3 moles, in the range of 0.4 to 1.3 moles, in the range of 0.5 to 1.3 moles, in the range of 0.5 to 1.2 moles, or in the range of 0.5 to 1.0 moles per mole of aluminum metal.

There is typically at least 0.1 mole of the second carboxylic acid per mole of aluminum present in the digestion mixture. In many embodiments, at least 0.2 moles, at least 0.3 moles, at least 0.4 moles, or at least 0.5 moles of the second carboxylic acid are present per mole of aluminum metal in the digestion mixture. For example, the amount of the second carboxylic acid can be in the range of 0.1 to 1.4 moles, in the range of 0.2 to 1.4 moles, in the range of 0.2 to 1.2 moles, in the range of 0.2 to 1.0 moles, or in the range of 0.2 to 0.8 moles per mole of aluminum metal.

There is generally no more than 0.2 mole of the third carboxylic acid per mole of aluminum metal in the digestion metal. The third carboxylic acid can decrease the solubility of the aluminum-containing precursor in the feedstock for the continuous hydrothermal reactor but may advantageously improve the compatibility of the resulting acicular boehmite nanoparticles with an organic matrix. In some embodiments, however, there is no third carboxylic acid added to the digestion mixture.

In some exemplary digestion mixtures, the aluminum concentration is in the range of 0.1 to 5 molar, the first carboxylic acid is present in an amount in the range of 0.1 to 1.4 moles per mole of aluminum, and the second carboxylic acid is present in an amount in the range of 0.1 to 1.4 moles per mole of aluminum. For example, the aluminum concentration can be in the range of 0.5 to 3 molar, the first carboxylic acid can be present in an amount in the range of 0.3 to 1.3 moles per mole of aluminum, and the second carboxylic acid can be present in an amount in the range of 0.2 to 1.2 moles per mole of aluminum. In other examples, the aluminum concentration can be in the range of 0.5 to 3 molar, the first carboxylic acid can be present in an amount in the range of 0.5 to 1.3 moles per mole of aluminum, and the second carboxylic acid can be present in an amount in the range of 0.2 to 1.0 moles per mole of aluminum. In any of these examples, there can be an optional third carboxylic acid in an amount up to 0.2 moles per mole of aluminum.

Expressed in terms of the aluminum-containing precursor of Formula (I), w is in the range of 1.5 to 2.2, x is in the range of 0.1 to 1.4, y is in the range of 0.1 to 1.4, and z is in the range of 0 to 0.2. In some examples, x is in the range of 0.3 to 1.3, y is in the range of 0.2 to 1.2, and z is in the range of 0 to 0.2. In other examples, x is in the range of 0.5 to 1.3, y is in the range of 0.2 to 1.0, and z is in the range of 0 to 0.2.

In some more specific examples, the aluminum concentration is in the range of 0.5 to 3 molar, the first carboxylic acid is formic acid that is present in an amount in the range of 0.5 to 1.3 moles per mole of aluminum, and the second carboxylic acid is acetic acid, propionic acid, or a mixture thereof that is present in an amount in the range of 0.2 to 1.0 moles per mole of aluminum. If a third carboxylic acid is present, it is present in an amount no greater than 0.2 moles per mole of aluminum. These specific examples correspond to an aluminum-containing precursor of Formula (I) where w is in the range of 1.5 to 2.2, x is in the range of 0.5 to 1.3, y is in the range of 0.2 to 1.0, and z is in the range of 0 to 0.2.

After digestion of the aluminum metal to prepare the aluminum-containing precursor of Formula (I), the digestion product is typically cooled to room temperature. The digestion product can be used directly as the feedstock solution for the continuous hydrothermal reactor. Alternatively, the digestion product can be diluted with water (e.g., deionized water) to lower the percent solids for use as the feedstock solution. Either with or without further dilution of the digestion product, the feedstock used for the continuous hydrothermal reactor typically is a solution. That is, the aluminum-containing precursor of Formula (I) is dissolved (i.e., not suspended or dispersed) in the feedstock solution.

Further, there is usually no aluminum-containing particulate matter included in the feedstock solution. If particles were in the feedstock, these particles may need to dissolve and then simultaneously undergo hydrolysis and condensation within the hydrothermal reactor. Such a process can be difficult to control because the rate of dissolution will depend on the size of the particles, the crystalline structure of the particles, and the surface characteristics of the particles in the feedstock. It can be difficult to control all of these parameters to prepare a consistent product. In contrast, a feedstock that is a solution can be easier to control and reproduce over time. That is, the product produced in the hydrothermal reactor can be more consistent over time when a feedstock solution is used. Additionally, the effluent of the hydrothermal reactor tends to contain fewer types of materials when a feedstock solution is used compared to when a feedstock containing particles is used.

In some embodiments, there can be a small amount of undissolved residue in the feedstock solution as prepared. This undissolved residue is often removed before the feedstock solution is passed through the continuous hydrothermal reactor. For example, the feedstock solution can be passed through one or more filters. Any known filter that can remove the undissolved residue can be used. In some embodiments, a paper filter such as those commercially available from Whatman International Ltd. (Maidstone, England) can be used. For example, paper filters such as a Whatman No. 50 filter or a Whatman No. 54 filter can be used for removing any undissolved residue. The feedstock solution can be passed through the filter by applying pressure or by drawing a vacuum on the receiving vessel.

The concentration of the feedstock solution is often expressed based on the aluminum concentration. The aluminum concentration of the feedstock solution is typically no greater than 5 molar. Higher concentrations can be difficult to pump through the continuous hydrothermal reactor. Additionally, more concentrated feedstocks are more likely to result in the deposition of materials on the walls of the continuous hydrothermal reactor leading to restricted flow through the reactor. This type of deposition can be minimized, however, by using a continuous hydrothermal reactor with a larger internal diameter or by using a longer continuous hydrothermal reactor at a higher flow rate. The aluminum concentration is often no greater than 4 molar, no greater than 3 molar, no greater than 2 molar, or no greater than 1 molar.

The concentration of aluminum in the feedstock solution is often selected to be as high as possible to maximize the efficiency of the process. In many embodiments, the concentration of aluminum is no less than 0.1 molar, no less than 0.2 molar, no less than 0.3 molar, no less than 0.4 molar, or no less than 0.5 molar. For example, the aluminum concentration is often in the range of 0.1 to 5 molar, in the range of 0.2 to 4 molar, in the range of 0.3 to 3 molar, in the range of 0.3 to 2 molar, in the range of 0.5 to 3 molar, or in the range of 0.5 to 2 molar.

The feedstock solution contains the aluminum-containing precursor of Formula (I) in an aqueous-based solvent. As used herein, the term "aqueous-based solvent" means that the solvent contains water and often is predominantly water. In addition to water, the aqueous-based solvent can contain, for example, a water-miscible solvent such as polar organic solvent as well as various dissolved carboxylic acids, anions of these dissolved carboxylic acids, or a mixture thereof. For example, the feedstock solution may contain dissolved carboxylic acids and/or anions thereof corresponding to those used to prepare the aluminum-containing precursor of Formula (I). That is, the feedstock solution may contain (a) a first carboxylic acid, an anion of the first carboxylic acid, or a mixture thereof and (b) a second carboxylic acid, an anion of the second carboxylic acid, or a mixture thereof. The first carboxylic acid is formic acid or acetic acid and the second carboxylic acid is acetic acid, propionic acid, butyric acid, or a mixture thereof. The first carboxylic acid is different than the second carboxylic acid. An optional third carboxylic acid having at least 5 carbon atoms, an anion of the optional third carboxylic acid, or a mixture thereof may also be present. The optional third carboxylic acid often is a mono-carboxylic acid having a poly(alkylene oxide) group. Some exemplary third carboxylic acids have 5 to 30 carbon atoms, 5 to 20 carbon atoms, 5 to 16 carbon atoms, or 5 to 12 carbon atoms.

Other materials can be added to the feedstock solution of the continuous hydrothermal reactor. For example, other acids such as other soluble, mono-carboxylic acids can be added. These additional acids may modify the surface of the resulting acicular boehmite nanoparticle. That is, these additional acids may sorb on the surface of the resulting acicular boehmite nanoparticle. In some embodiments, an additional mono-carboxylic acid having a polyalkylene oxide group can be added to the feedstock solution. The polyalkylene oxide group contains repeating alkylene oxide units of the general formula —O—R— where R is an alkylene group such as, for example, methylene, ethylene and propylene (including n-propylene and iso-propylene) or a combination thereof. Suitable poly(alkylene oxide)-containing carboxylic acids usually have at least five carbon atoms and can be of Formula (II). Some exemplary poly(alkylene oxide)-containing carboxylic acids have 5 to 30 carbon atoms, 5 to 20 carbon atoms, 5 to 16 carbon atoms, or 5 to 12 carbon atoms. Exemplary poly(alkylene oxide) carboxylic acids include, but are not limited to, 2-[2-(2-methoxyethoxy)ethoxy]acetic acid (MEEAA) and 2-(2-methoxyethoxy)acetic acid (MEAA). In other embodiments, the additional mono-carboxylic acid can be an alpha-hydroxyl acid. The alpha-hydroxyl acid often has a single carboxyl group and up to 20 carbon atoms. The alpha-hydroxyl acid often contains up to 16 carbon atoms, up to 12 carbon atoms, up to 8 carbon atoms, up to 6 carbon atoms, or up to 4 carbon atoms. Exemplary alpha-hydroxyl acids include, but are not limited to, lactic acid and glycolic acid. These modifying acids, if included in the feedstock solution, are typically present in an amount no greater than 0.2 moles per mole of aluminum, no greater than 0.1 mole per mole of aluminum. or not greater than 0.05 moles per mole of aluminum.

If these additional acids are added to the feedstock, longer residence times may be needed within the continuous hydrothermal reactor to produce the acicular boehmite nanoparticles. However, the use of these additional acids may be desirable if the resulting acicular boehmite nanoparticles will be subsequently dispersed or suspended in an organic matrix. The additional acids tend to sorb on the surface of the boehmite nanoparticles rendering them more compatible with the organic matrix, with various surface modification agents, or with both.

The pH of the feedstock solution is typically no greater than 6. If the pH is higher than 6, acicular shaped acicular boehmite nanoparticles typically are not formed during the hydrolysis and condensation reactions within the continuous hydrothermal reactor. The pH is often no greater than 5.5 or no greater than 5. The pH can be in the range of 3 to 6, in the range of 3 to 5, or close to 4. The pH of the feedstock solution can be lowered, if necessary, by the addition of a soluble mono-carboxylic acid.

The feedstock solution typically does not contain nitrate ions or halide ions. That is, the feedstock solution is typically free or substantially free of halide and nitrate ions. As used herein, the term "substantially free" with reference to halide and nitrate ions means that these ions are not intentionally added but may be present as impurities in other components of the feedstock solution. Any nitrate ions sorbed on the formed acicular boehmite nanoparticles or remaining when the acicular boehmite nanoparticles are suspended or dispersed in an organic matrix may result in the undesirable oxidation of the organic matrix. Halides, on the other hand, tend to be quite corrosive and can be incompatible with the organic matrix. If the boehmite is used to prepare a ceramic material, the presence of halides can be particularly undesirable. The feedstock solution contains no greater than 10 millimolar, no greater than 5 millimolar, no greater than 1 millimolar, or no greater than 0.5 millimolar halide or nitrate. That is, the concentration of halide or nitrate in the feedstock solution is in the range of 0 to 10 millimolar, in the range of 0 to 5 millimolar, in the range of 0 to 1 millimolar, or in the range of 0 to 0.5 millimolar.

The feedstock solution is passed through a continuous hydrothermal reactor. Any known design of a continuous hydrothermal reactor can be used. For example, some suitable continuous hydrothermal reactors are described in an article by Adschiri et al., *J. Am. Ceram. Soc.*, 75 (4), 1019-1022 (1992) and in U.S. Pat. No. 5,453,262 (Dawson et al). In these designs, the portion of the continuous hydrothermal reactor system that is heated includes a tube that is straight and that has a surrounding electrical-resistance heater.

One exemplary continuous hydrothermal reactor system 100 is shown schematically in FIG. 1. The feedstock solution 110 is contained within a feedstock solution tank 115. The feedstock solution tank is connected with tubing or piping 117 to a pump 120. Similar tubing or piping can be used to connect other components of the hydrothermal reactor system. The tubing or piping 117 can be constructed of any suitable material such as metal, polymer, glass, or ceramic. In some embodiments, the tubing or piping 117 can be polyethylene tubing or polypropylene tubing in the portions of the continuous hydrothermal reactor system 100 that are not heated and that are not under high pressure. The pump 120 is used to introduce the feedstock solution 110 into the tubular reactor 130. That is, the pump 120 is connected to the inlet of the tubular reactor 130. Any type of pump 120 can be used that is capable of pumping against the pressure within the tubular reactor 130. The pump can provide a constant or pulsed flow of the feedstock solution into the tubular reactor 130.

As used herein, the term "tubular reactor" refers to the portion of the continuous hydrothermal reactor system that is heated (i.e., the heated zone). Although the tubular reactor 130 is shown in FIG. 1 as a coil of tubing, the tubular reactor can have any suitable shape. The shape of the tubular reactor is often selected based on the desired length of the tubular reactor and the method used to heat the tubular reactor. For example, the tubular reactor can be straight, U-shaped, or coiled. The interior potion of the tubular reactor can be empty or can contain baffles, balls, or other known mixing means.

As shown in FIG. 1, the tubular reactor 130 is placed in a heating medium 140 within a heating medium vessel 150. The heating medium 140 can be, for example, an oil, sand, salt, or the like that can be heated to a temperature above the hydrolysis and condensation temperatures of the aluminum-containing precursor of Formula (I). Suitable oils include, for example, plant oils such as peanut oil and canola oil. Some plant oils are preferably kept under nitrogen when heated to prevent or minimize oxidation of the oils. Other suitable oils include polydimethylsiloxanes such as those commercially available from Duratherm Extended Fluids (Lewiston, N.Y.) under the trade designation "DURATHERM S". Suitable salts include, for example, sodium nitrate, sodium nitrite, potassium nitrate, or mixtures thereof. The heating medium vessel 150 can be any suitable container that can hold the heating medium and withstand the heating temperatures used for the tubular reactor 130. The heating medium vessel 150 can be heated using any suitable means. In many embodiments, the heating medium vessel 150 is positioned inside an electrically heated coil. Alternatively, other types of heaters such as, for example, induction heaters, microwave heaters, fuel-fired heaters, heating tape, and steam coils can be used in place of the heating vessel 150, the heating medium 140, or both.

The tubular reactor 130 can be made of any material capable of withstanding the temperatures and pressures used to prepare acicular boehmite nanoparticles. The tubular reactor 130 preferably is constructed of a material that can resist dissolution in the presence of an acidic environment. For example, carboxylic acids can be present in the feedstock or can be produced as a reaction byproduct within the continuous hydrothermal reactor system. In some exemplary embodiments, the tubular reactor is made of stainless steel, nickel, titanium, carbon-based steel, or the like.

In other exemplary embodiments, an interior surface of the tubular reactor contains a fluorinated polymeric material. This fluorinated polymeric material can include, for example, a fluorinated polyolefin. In some embodiments, the fluorinated polymeric material is polytetrafluoroethylene (PTFE) such as TEFLON, which is a trade designation of DuPont (Wilmington, Del.). Some tubular reactors have a fluorinated polymeric hose such as a PTFE hose within a metal housing such as a braided stainless steel housing. Surprisingly, the heat transfer is typically sufficient through the fluorinated polymeric material to convert the aluminum-containing precursor in the feedstock solution to acicular boehmite nanoparticles under continuous hydrothermal conditions. The fluorinated polymeric surface is particularly advantageous for use with feedstock solutions and/or reaction products that contain carboxylic acids. These carboxylic acids can leach metals from some known hydrothermal reactors such as those constructed of stainless steel.

The second end of the tubular reactor 130 is usually connected to a cooling device 160. Any suitable cooling device 160 can be used. In some embodiments, the cooling device 160 is a heat exchanger that includes a section of tubing or piping with an outer jacket filled with a cooling medium such as cool water. In other embodiments, the cooling device 160 includes a coiled section of tubing or piping that is placed in a vessel that contains cooling water. In either of these embodiments, the reactor effluent is passed through the section of tubing and is cooled from the tubular reactor temperature to a temperature no greater than 100° C., no greater than 80° C., no greater than 60° C., or no greater than 40° C. Other cooling devices that contain dry ice or refrigeration coils can also be used. After cooling, the reactor effluent can be discharged into a product collection vessel 180. The tubular reactor effluent is preferably not cooled below the freezing point prior to being discharged into the product collection vessel 180.

The pressure inside the tubular reactor can be at least partially controlled with a backpressure valve 170, which is generally positioned between the cooling device 160 and the sample collection vessel 180. The backpressure valve 170 controls the pressure at the exit of the continuous hydrothermal reactor system 100 and helps to control the pressure within the tubular reactor 130. The backpressure is often at least 100 pounds per square inch (0.7 MPa), at least 200 pounds per square inch (1.4 MPa), at least 300 pounds per square inch (2.1 MPa), at least 400 pounds per square inch (2.8 MPa), at least 500 pounds per square inch (3.5 MPa), at least 600 pounds per square inch (4.2 MPa), or at least 700 pounds per square inch (4.9 MPa). The backpressure should be high enough to prevent boiling within the tubular reactor 130.

The dimensions of the tubular reactor 130 can be varied and, in conjunction with the flow rate of the feedstock solution, can be selected to provide suitable residence times for the reactants within the tubular reactor. As used herein, the term "residence time" refers to the average length of time that the feedstock is within the heated zone of the continuous hydrothermal reactor system. That is, the residence time is the average time the feedstock is within the tubular reactor 130 and is equal to the tubular reactor volume divided by the flow rate of the feedstock solution. Any suitable length tubular reactor can be used provided that the residence time is sufficient to convert the aluminum-containing precursor to acicular boehmite nanoparticles. The tubular reactor often has a length of at least 0.5 meter, at least 1 meter, at least 2 meters, at least 5 meters, at least 10 meters, at least 15 meters, at least 20 meters, at least 30 meters, at least 40 meters, or at least 50 meters. The length of the tubular reactor in some embodiments is less than 500 meters, less than 400 meters, less than 300 meters, less than 200 meters, less than 100 meters, less than 80 meters, less than 60 meters, less than 40 meters, or less than 20 meters.

Tubular reactors with a relatively small inner diameter are typically preferred. For example, tubular reactors having an inner diameter no greater than about 3 centimeters are often used because a relatively fast rate of heating of the feedstock solution can be achieved with these reactors. Also, the temperature gradient across the tubular reactor is smaller for reactors with a smaller inner diameter compared to those with a larger inner diameter. The larger the inner diameter of the tubular reactor, the more this reactor undesirably resembles a batch reactor. However, if the inner diameter of the tubular reactor is too small, there is an increased likelihood of the reactor becoming plugged or partially plugged during operation resulting from deposition of material on the walls of the reactor. The inner diameter of the tubular reactor is often at least 0.1 centimeters, at least 0.15 centimeters, at least 0.2 centimeters, at least 0.3 centimeters, at least 0.4 centimeters, at least 0.5 centimeters, or at least 0.6 centimeters. In some embodiments, the diameter of the tubular reactor is no greater than 3 centimeters, no greater than 2.5 centimeters, no greater than 2 centimeters, no greater than 1.5 centimeters, or no greater than 1.0 centimeters. Some tubular reactors have an inner diameter in the range of 0.1 to 3.0 centimeters, in the range of 0.2 to 2.5 centimeters, in the range of 0.3 to 2 centimeters, in the range of 0.3 to 1.5 centimeters, or in the range of 0.3 to 1 centimeter.

Rather than increasing the inner diameter of the tubular reactor, it may be preferable to use multiple tubular reactors having a smaller inner diameter arranged in a parallel manner. For example, rather than increasing the inner diameter of the tubular reactor to produce a larger amount of acicular boehmite nanoparticle, multiple tubular reactors having an inner diameter no greater than about 3 centimeters can be operated in parallel.

Any suitable flow rate of the feedstock through the tubular reactor can be used as long as the residence time is sufficiently long to convert the aluminum-containing precursor to acicular boehmite nanoparticles. Higher flow rates are desirable for increasing throughput and minimizing the deposition of materials on the walls of the tubular reactor. The flow rate is often selected based on the residence time needed to convert the aluminum-containing precursor to acicular boehmite nanoparticles. A higher flow rate can often be used when the length of the tubular reactor is increased or when both the length and diameter of the tubular reactor are increased. The flow through the tubular reactor can be either laminar or turbulent.

The tubular reactor is held at a temperature that is greater than the hydrolysis and condensation reaction temperatures of the aluminum-containing precursor. The temperature is often at least 130° C., at least 140° C., or at least 150° C. In some embodiments, the aspect ratio of the resulting acicular boehmite nanoparticle tends to decrease when the reactor temperature is increased. If the temperature is too high, the pressure of the tubular reactor may be unacceptably high. The temperature is typically no greater than 230° C., no greater then 225° C., or no greater than 220° C. In many embodiments, the reaction temperature is selected to be in the range of 130° C. to 230° C., in the range of 140° C. to 220° C., in the range of 140° C. to 200° C., in the range of 150° C. to 200° C., or in the range of 150° C. to 180° C.

The residence time in the tubular reactor can be varied by altering the length or diameter of the tubular reactor as well as by altering the flow rate of the feedstock solution. In many embodiments, the residence time is at least 2 minutes, at least 4 minutes, at least 6 minutes, at least 8 minutes, or at least 10 minutes. The residence time is typically no greater than 90 minutes, no greater than 60 minutes, no greater than 50 minutes, no greater than 40 minutes, or no greater than 30 minutes. In many examples, the residence time is in the range of 2 to 90 minutes, in the range of 2 to 60 minutes, in the range of 5 to 60 minutes, in the range of 5 to 50 minutes, in the range of 5 to 40 minutes, in the range of 5 to 30 minutes, in the range of 10 to 30 minutes, or in the range of 10 to 20 minutes.

The effluent of the continuous hydrothermal reactor contains acicular boehmite nanoparticles. The acicular boehmite nanoparticles are dispersed or suspended in an aqueous-based solvent. This aqueous-based solvent often contains dissolved carboxylic acids and/or anions thereof that are present in the feedstock solution, that are byproducts of the reactions that occur within the tubular reactors, or both. As used herein, the phrase "carboxylic acid and/or anions thereof" refers to a carboxylic acid, an anion of the carboxylic acid (i.e., the carboxylate anion corresponding to the carboxylic acid), or a mixture thereof. The effluent often contains (a) a dissolved first carboxylic acid and/or an anion thereof and (b) a dissolved second carboxylic acid and/or an anion thereof. The first carboxylic acid is formic acid or acetic acid. The second carboxylic acid, which is different than the first carboxylic acid, is acetic acid, propionic acid, butyric acid, or a mixture thereof. The effluent can also contain an optional dissolved third carboxylic acid having at least 5 carbon atoms, an anion of the optional third carboxylic acid, or a mixture thereof.

The effluent from the hydrothermal reactor can be clear or slightly turbid depending on the size of the particles and the degree of agglomeration. Turbidity increases with an increase in the average particle size and with an increase in the extent of agglomeration. As it exits the hydrothermal reactor system, the effluent is typically fluid (e.g., the viscosity is less then 300 centipoises, less than 200 centipoises, less than 150 centipoises, or less than 100 centipoises). If the effluent is not treated to remove various dissolved salts from the effluent, the viscosity can increase over time and the effluent can become a gel. Depending on the concentration of the effluent, the gel can form within minutes or hours. Gels tend to form more quickly from more concentrated effluents.

For many applications, removal of at least some of the aqueous-based solvent from the effluent of the hydrothermal reactor is desirable. In particular, removal of at least a portion of the water in the aqueous-based solvent can be desirable. Any suitable means known in the art can be used to remove at least a portion of the water. For example, methods such as vaporization, drying, and solvent exchange can be used. The removal of at least some of the water can be accompanied by the removal of at least a portion of the dissolved carboxylic acids and/or anions thereof. For example, the removal of at least some of the water in the effluent may be accompanied by the removal of at least a portion of the first carboxylic acid and/or anion thereof plus the removal of at least a portion of the second carboxylic acid and/or anion thereof.

In some embodiments, at least a portion of the water in the effluent from the continuous hydrothermal reactor can be removed by drying the effluent. The drying process can also result in the vaporization of at least some of the carboxylic acids such as those having no more than 4 carbon atoms. Any suitable drying method can be used such as spray drying, gap drying, or oven drying. For example, the effluent can be dried in a conventional oven at a temperature of at least 80° C., at least 90° C., at least 100° C., at least 110° C., or at least 120° C. The drying time is often greater than 30 minutes, greater than 1 hour, greater than 2 hours, or greater than 3 hours.

In still other embodiments, at least a portion of the water in the effluent of the continuous hydrothermal reactor can be removed using a solvent exchange method. An organic solvent with a higher boiling point than water can be added to the effluent. Examples of organic solvents that are suitable for use in a solvent exchange method include, but are not limited to, 1-methoxy-2-propanol and N-methylpyrrolidone. The mixture containing the effluent plus the organic solvent can be treated to remove the water using methods such as, for example, distillation, rotary evaporation, or oven drying. Depending on the conditions, at least a portion of the dissolved carboxylic acids and/or anions thereof also may be removed by the solvent exchange method.

In some applications, it may be desirable to remove at least a portion of the dissolved carboxylic acids and/or anions thereof in the effluent of the continuous hydrothermal reactor. Removal of at least a portion of the dissolved carboxylic acids and/or anions thereof may be desirable to minimize formation of a gel or when the acicular boehmite nanoparticles will be suspended or dispersed in an organic matrix. Any known method can be used to remove the dissolved carboxylic acids and/or anions thereof. For example, these species can be removed using dialysis, diafiltration, or an anion exchange resin.

If dialysis is used to remove at least a portion of the dissolved carboxylic acids and/or anions thereof in the effluent of the hydrothermal treatment, a sample of the effluent can be positioned within a membrane bag that is closed and then placed within a water bath. A membrane bag is typically selected that allows diffusion of the carboxylic acids and/or anions thereof but does not allow diffusion of the acicular boehmite nanoparticles out of the membrane bag. The carboxylic acid and/or carboxylate anions diffuse out of the sample within the membrane bag. That is, these species will diffuse out of the effluent within the membrane bag into the water bath to equalize the concentration within the membrane bag to the concentration in the water bath. The water in the bath is typically replaced several times to lower the concentration of species within the bag.

For diafiltration, a permeable membrane is used to filter the sample. The acicular boehmite nanoparticles can be retained on the filter if the pore size of the filter is appropriately chosen. The dissolved carboxylic acids and/or anions thereof pass through the filter. Any liquid that passes through the filter is replaced with fresh water. In a discontinuous diafiltration process, the sample is often diluted to a pre-determined volume and then concentrated back to the original volume by ultrafiltration. The dilution and concentration steps are repeated one or more times until the carboxylic acid and/or anions thereof are removed or lowered to an acceptable concentration level. In a continuous diafiltration process, which is often referred to as a constant volume diafiltration process, fresh water is added at the same rate that liquid is removed through filtration. The dissolved carboxylic acid and/or anions thereof are in the liquid that is removed.

At least a portion of the dissolved carboxylic acid and/or anions thereof in the effluent of the continuous hydrothermal reactor also can be removed using an anion exchange resin in a hydroxyl form. By adjusting the pH of the effluent, the carboxylic acids can be converted to the basic form (i.e., carboxylate anion). At least some of the carboxylate anions can replace some of the hydroxyl ions on the anion exchange resin. The pH adjusted effluent can be passed through a column containing the anion exchange resin or through a filtration medium containing the anion exchange resin. Alternatively, the anion exchange resin can be mixed with the effluent of the continuous hydrothermal reactor. After ion exchange, the anion exchange resin can be removed by filtration. The size of the anion exchange resin is selected so that it can be easily filtered from the treated effluent. For example, the size of the anion exchange resin is often no greater than 200 mesh, no greater than 100 mesh, or no greater than 50 mesh.

The acicular boehmite nanoparticles in the effluent from the continuous hydrothermal reactor usually contain sorbed carboxylic acids, salts of the carboxylic acids, or mixtures thereof (i.e., sorbed modifiers). These sorbed carboxylic acids and/or anions thereof typically are not removed by the treatments used to remove the dissolved carboxylic acid and/or anions thereof in the effluent. Although it may be desirable to remove the carboxylic acids and/or anions thereof that are dissolved in the effluent of the continuous hydrothermal reactor, it may be advantageous to have these same moieties sorbed on the surface of the acicular boehmite nanoparticle. These sorbed carboxylic acids and/or anions thereof can function as surface modifiers that can enhance compatibility of the acicular boehmite nanoparticles with various organic matrix materials.

The sorbed modifiers on a surface of the acicular boehmite nanoparticle include (a) a first carboxylic acid and/or anion thereof and (b) a second carboxylic acid and/or anion thereof. The first carboxylic acid is selected from formic acid or acetic acid. The second carboxylic acid, which is different than the first carboxylic acid, is selected from acetic acid, formic acid, propionic acid, butyric acid, or a mixture thereof. In some embodiments, the first carboxylic acid is formic acid and the second carboxylic acid is acetic acid, propionic acid, or mixtures thereof. There can be an optional third carboxylic acid and/or anion thereof having at least five carbon atoms sorbed on the surface of the acicular boehmite nanoparticle. The optional third carboxylic acid and/or anion thereof often has 5 to 30 carbon atoms and has a poly(alkylene oxide) group.

The acicular boehmite nanoparticles often contain at least 0.5 weight percent carboxylic acids and/or anions thereof sorbed on the surface. For example, the acicular boehmite nanoparticle can contain at least 1.0 weight percent, at least 1.5 weight percent, at least 2 weight percent, at least 3 weight percent, at least 4 weight percent, or at least 5 weight percent carboxylic acids or anions thereof based on the weight of the acicular boehmite nanoparticle.

The boehmite prepared within the continuous hydrothermal reactor system is an acicular nanoparticle. The average aspect ratio is at least 3:1. As used herein, the term "aspect ratio" refers to the ratio of the length of the boehmite nanoparticle to the width of the boehmite nanoparticle. In some embodiments, the average aspect ratio is at least 4:1, at least 5:1, at least 6:1, at least 8:1, or at least 10:1. A large aspect ratio is desirable for many applications because fewer acicular boehmite nanoparticles need to be added to produce the desired effect. For example, the amount of the acicular boehmite nanoparticles needed to produce a composite material with a desired tensile strength can be lowered by increasing the aspect ratio of the acicular boehmite nanoparticles. The dimensions of the acicular boehmite nanoparticle can be measured, for example, by measuring at least 50 particles on a transmission electron micrograph.

The acicular boehmite nanoparticles usually have an average length no greater than 1000 nanometers, no greater than 500 nanometers, no greater than 400 nanometers, no greater than 300 nanometers, no greater than 200 nanometers, or no greater than 100 nanometers. The average length is typically at least 5 nanometers, at least 10 nanometers, at least 20 nanometers, at least 30 nanometers, at least 40 nanometers, or at least 50 nanometers. For example, the average length can be in the range of 5 to 500 nanometers, in the range of 20 to 500 nanometers, in the range of 10 to 400 nanometers, in the range of 20 to 400 nanometers, in the range of 10 to 300 nanometers, in the range of 10 to 200 nanometers, or in the range of 10 to 100 nanometers.

The average particle width is typically no greater than 20 nanometers, no greater than 15 nanometers, no greater than 12 nanometers, no greater than 10 nanometers, no greater than 8 nanometers, no greater than 6 nanometers, or no greater than 5 nanometers. The average width, for example, can be in the range of 1 to 20 nanometers, in the range of 1 to 15 nanometers, in the range of 1 to 10 nanometers, or in the range of 2 to 10 nanometers.

The acicular boehmite nanoparticles typically are crystalline as determined using x-ray diffraction. The acicular boehmite nanoparticles are often substantially non-associated or can be dispersed to be substantially non-associated. As used herein, the term "non-associated" means that the particles are substantially free of aggregation and/or agglomeration. Aggregation refers to a strong association between primary particles such as a chemical bond. Agglomeration refers to a weaker association between primary particles such as polar attraction. The breakdown of agglomerates into smaller particles such as the primary particles is less difficult than the breakdown of aggregates.

In yet another aspect, a composite material is provided that includes an organic matrix and acicular boehmite nanoparticles dispersed or suspended in the organic matrix. Various sorbed modifiers are on a surface of the acicular boehmite nanoparticle. The sorbed modifiers include (a) a first carboxylic acid, an anion of the first carboxylic acid, or a mixture thereof and (b) a second carboxylic acid, an anion of the second carboxylic acid, or a mixture thereof. The first carboxylic acid is selected from formic acid or acetic acid. The second carboxylic acid, which is different than the first carboxylic acid, is selected from acetic acid, formic acid, propionic acid, butyric acid, or a mixture thereof. There can be an optional third carboxylic acid and/or anion thereof having at least five carbon atoms sorbed on the surface of the acicular boehmite nanoparticle. The optional third carboxylic acid and/or anion thereof often has 5 to 30 carbon atoms and has a poly(alkylene oxide) group.

The effluent from the hydrothermal reactor contains acicular nanoparticles that have sorbed carboxylic acids. In some applications, the acicular boehmite nanoparticles are compatible with the organic matrix without any further surface modification. In other applications, however, the acicular boehmite nanoparticle is further treated with an additional surface modification agent to further improve compatibility with the organic matrix material.

Surface modification agents may be represented by the formula A-B where the A group is capable of attaching to the surface of an acicular boehmite nanoparticle and B is a compatibility group. Group A can be attached to the surface by adsorption, formation of an ionic bond, formation of a covalent bond, or a combination thereof. Group B can be reactive or non-reactive and often tends to impart characteristics to the acicular boehmite nanoparticles that are compatible (i.e., miscible) with an organic solvent, with an organic matrix material, or both. For example, if the solvent is non-polar, group B is typically selected to be non-polar as well. Suitable B groups include linear or branched hydrocarbons that are aromatic, aliphatic, or both aromatic and aliphatic. The surface modifying agents include, but are not limited to, carboxylic acids and/or anions thereof, sulfonic acids and/or anions thereof, phosphoric acids and/or anions thereof, phosphonic acids and/or anions thereof, silanes, amines, and alcohols.

In some embodiments, the surface modification agent is a carboxylic acid and/or anion thereof and the compatibility B group can impart a polar character to the acicular boehmite nanoparticles. For example, the surface modification agent can be a carboxylic acid and/or anion thereof having a polyalkylene oxide group. Representative examples include 2-[2-(2-methoxyethoxy)ethoxy]acetic acid (MEEAA), 2-(2-methoxyethoxy)acetic acid (MEAA), and mono(polyethylene glycol)succinate.

In other embodiments, the surface modification agent is a carboxylic acid and/or anion thereof and the compatibility B group can impart a non-polar character to the acicular boehmite nanoparticles. For example, the surface modification agent can be a carboxylic acid and/or anion thereof having a linear or branched aromatic group or aliphatic hydrocarbon group. Representative examples of include octanoic acid, dodecanoic acid, stearic acid, oleic acid, and combinations thereof.

In still other embodiments, the surface modification agent is a carboxylic acid and/or anion thereof and the compatibility B group can be reactive with a polymerizable organic matrix (e.g., the B group contains a polymerizable group). Reactive carboxylic acid surface modifying agents (e.g., carboxylic acids with polymerizable groups) include, for example, acrylic acid, methacrylic acid, beta-carboxyethyl acrylate, mono-2-(methacryloxyethyl)succinate, and combinations thereof. A useful surface modification agent that can impart both polar character and reactivity to the acicular boehmite nanoparticles is mono(methacryloxypolyethyleneglycol)succinate. This material may be particularly suitable for addition to radiation curable acrylate and/or methacrylate organic matrix materials.

Exemplary silane surface modification agents include, but are not limited to, alkyltrialkoxysilanes such as n-octyltrimethoxysilane, n-octyltriethoxysilane, isooctyltrimethoxysilane, dodecyltrimethoxysilane, octadecyltrimethoxysilane, propyltrimethoxysilane, and hexyltrimethoxysilane; methacryloxyalkyltrialkoxysilanes or acryloxyalkyltrialkoxysilanes such as 3-methacryloxypropyltrimethoxysilane, 3-acryloxypropyltrimethoxysilane, and 3-(methacryloxy)propyltriethoxysilane; methacryloxyalkylalkyldialkoxysilanes or acryloxyalkylalkyldialkoxysilanes such as 3-(methacryloxy)propylmethyldimethoxysilane, and 3-(acryloxypropyl)methyldimethoxysilane; methacryloxyalkyldialkylalkoxysilanes or acyrloxyalkyldialkylalkoxysilanes such as 3-(methacryloxy)propyldimethylethoxysilane; mercaptoalkyltrialkoxylsilanes such as 3-mercaptopropyltrimethoxysilane; aryltrialkoxysilanes such as styrylethyltrimethoxysilane, phenyltrimethoxysilane, phenyltriethoxysilane, and p-tolyltriethoxysilane; vinyl silanes such as vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, vinyltriphenoxysilane, vinyltri-t-butoxysilane, vinyltris(isobutoxy)silane, vinyltriisopropenoxysilane, and vinyltris(2-methoxyethoxy)silane; 3-glycidoxypropyltrialkoxysilane such as glycidoxypropyltrimethoxysilane; polyether silanes such as N-(3-triethoxysilylpropyl)methoxyethoxyethyl carbamate (PEG3TES), N-(3-triethoxysilylpropyl)methoxyethoxyethoxyethyl carbamate (PEG2TES), and SILQUEST A-1230; and combinations thereof.

Whether or not an additional surface modification agent is added to the surface of the acicular boehmite nanoparticles, at least a portion of the water in the effluent of the hydrothermal reactor is often removed prior to mixing the acicular boehmite nanoparticles with an organic matrix. In some examples, the effluent from the continuous hydrothermal reactor can be dried at a temperature suitable for removing water plus at least a portion of the dissolved carboxylic acid and/or anions thereof. If no additional surface modification agent is added, the dried acicular boehmite nanoparticle can be suspended or dispersed in an organic matrix. When the dried acicular boehmite nanoparticle is mixed with the organic matrix, an optional organic solvent can be present that may be subsequently removed.

If an additional surface modification agent is added, the dried acicular boehmite nanoparticle can be mixed initially with the surface modification agent in an optional organic solvent. After surface treatment, the surface modified acicular boehmite nanoparticle can be mixed with an organic matrix. The optional organic solvent can be removed before or after addition of the organic matrix. Alternatively, if an additional surface modification agent is added, the dried acicular boehmite nanoparticle can be mixed with both the organic matrix and the surface modification agent in the presence of an optional organic solvent. The optional organic solvent can be removed after surface modification.

In another example, at least a portion of the water can be removed from the effluent of the continuous hydrothermal reactor by a solvent exchange process. An organic solvent having a higher boiling point than water is added to the effluent. The water can be removed by a method such as, for example, distillation, rotary evaporation, oven drying, or the like. Depending on the conditions used for removing the water, at least a portion of the dissolved carboxylic acid and/or anion thereof also can be removed. If no additional surface modification agent is added, the organic matrix can be added to the treated effluent (i.e., the organic matrix is added to the acicular boehmite nanoparticle suspended in the organic solvent used in the solvent exchange process).

If an additional surface modification agent is added, the additional surface modification agent can be added either before or after the solvent exchange process. The surface modification agent can be selected to facilitate the extraction of the acicular boehmite nanoparticles in to the organic solvent used in the solvent exchange process. The organic matrix can be added after the solvent exchange process. Alternatively, the organic matrix, organic solvent, and the additional surface modification agent can be added at the same time. The organic solvent used in the solvent exchange process can often be removed after addition of the organic matrix using a method such as distillation, rotary evaporation, oven drying, or the like.

In some applications, the organic solvent, the organic matrix, and a surface modification agent are all mixed with the effluent of the hydrothermal reactor. The water and organic solvent are then removed by distillation. At least some of the dissolved carboxylic acid and/or anions thereof in the effluent are also removed during distillation.

In yet another example, the dissolved carboxylic acid and/or anion thereof in the effluent from the continuous hydrothermal reactor can be removed by a process such as dialysis or ion exchange. If no additional surface modification agent is added, an organic matrix can be added either before or after removal of most of the water from the treated effluent. If the organic matrix is added before removal of most of the water and the boiling point of the organic matrix is greater than the boiling point of water, the water can be removed using a method such as distillation, rotary evaporation, or oven drying. Alternatively, the pH of the treated effluent can be adjusted to precipitate the acicular boehmite nanoparticle. The precipitated acicular boehmite nanoparticle can be collected by filtration or centrifugation. Any remaining water can be removed either before or after mixing the filtered or centrifuged acicular boehmite nanoparticle with an organic matrix.

If an additional surface modification agent is used, this additional surface modification agent can be added directly to the effluent treated using ion exchange or dialysis or to untreated effluent. Optionally, a polar co-solvent may be added to increase the solubility of the surface modification agent in the aqueous phase. Suitable polar co-solvents include water-miscible organic compounds such as, for example, 1-methoxy-2-propanol, ethanol, isopropanol, ethylene glycol, N,N-dimethylacetamide, N-methyl pyrrolidone, or the like. The organic matrix can be added either before or after removal of most of the water and optional polar co-solvents. The water and optional polar co-solvent can be removed, for example, by distillation, rotary evaporation, or oven drying if the organic matrix has a higher boiling point. The water and optional polar co-solvent can also be removed by precipitation of the surface modified acicular boehmite nanoparticle by adjusting the pH. Alternatively, the surface modification agent can change the polarity of the acicular boehmite nanoparticles resulting in the precipitation of the surface modified acicular boehmite nanoparticles. The precipitated acicular boehmite nanoparticle can be separated from the liquid phase by filtration or centrifugation. Any remaining water and optional co-solvent can be removed either before or after mixing the filtered or centrifuged acicular boehmite nanoparticle with an organic matrix.

Alternatively, if an additional surface modification agent is added, both the surface modification agent and the organic matrix can be added directly to untreated effluent or effluent treated using ion exchange or dialysis. An optional polar co-solvent can be added. After addition of the organic matrix, the water and optional polar co-solvent can be removed, for example, by distillation, rotary evaporation, oven drying, or the like. As another alternative, the treated effluent can be dried before combination with an additional surface modification agent, organic matrix, or both. In this alternative, the surface modification agent can be added with an optional organic solvent either before or concurrently with the addition of the organic matrix.

The surface modification reactions can occur at room temperature (e.g., 20° C. to 25° C.) or at an elevated temperature (e.g., up to about 95° C.). When the surface modification agents are acids such as carboxylic acids, the acicular boehmite nanoparticles typically can be surface-modified at room temperature. When the surface modification agents are silanes, the acicular boehmite nanoparticles are typically surface modified at elevated temperatures.

The organic matrix typically includes a polymeric material or a precursor to a polymeric material such as a monomer or a oligomer having a polymerizable group. Any suitable technique can be used to combine the acicular boehmite nanoparticles with the organic matrix. For example, if the organic matrix is a precursor to a polymeric material, the acicular boehmite nanoparticles can be added prior to the polymerization reaction. If the polymeric material is a thermoplastic, the polymeric material and the acicular boehmite nanoparticles can be combined using a process such as extrusion, milling or Brabender mixing. The composite material containing a precursor of a polymeric material is often shaped or coated before polymerization.

Representative examples of monomers include, but are not limited to, (meth)acrylates, styrenes, epoxies, and the like. Representative examples of reactive oligomers include, but are not limited to, (meth)acrylated polyesters, (meth)acrylated polyurethanes, or acrylics. Representative examples of polymeric material include, but are not limited to, polyolefins, polyesters, polyurethanes, poly(meth)acrylates, polystyrenes, polycarbonates, and polyimides.

One exemplary process for forming a composite material includes concentrating the effluent from the hydrothermal reactor to about 40 percent solids or more using a method such as distillation or rotary evaporation. A co-solvent and surface modification agent can be added to the concentrate. After addition of the organic matrix, the co-solvent, and water are removed. At least a portion of the dissolved carboxylic acid and/or anion thereof can be removed during the concentration step or after surface modification.

The addition of the acicular boehmite nanoparticles to an organic matrix such as a polymeric material can be advantageous. For example, the acicular boehmite nanoparticles can be added to increase the tensile strength of a polymeric material or can be added as a thickener to an organic matrix. Because the nanoparticles can be smaller than the wavelengths of visible light, their presence in an organic matrix often cannot be detected with the unaided eye. That is, the tensile strength or thickness of an organic matrix can be increased without affecting the appearance of the organic matrix. For example, the acicular boehmite nanoparticles can be suspended or dispersed in an organic matrix for applications where a high optical transmission is desired.

EXAMPLES

Test Methods

High-Resolution Thermogravimetric Analysis

The acicular boehmite nanoparticle samples were analyzed using the TA Instruments 2950 Thermogravimetric Analyzer (TGA), which is commercially available from TA Instruments (New Castle, Del.). Each sample was placed on a weighed platinum thermogravimetric analysis pan. A linear heating rate of 10° C./min was applied with a resolution setting of 4.0. Under these conditions, the instrument heated the sample until weight loss was detected. The temperature was held constant until the weight loss diminished and then the temperature was increased again. The samples were subjected to a heating profile ranging from room temperature to 1000° C. in a nitrogen atmosphere. The TGA data analyses include the weight loss step analysis results, and the residual weight after the test cycle was complete.

Headspace GC/MS Analysis Method

Roughly 0.1 grams of each acicular boehmite nanoparticle sample was sealed in a separate 20 milliliter headspace vial. The vials were heated for 60 minutes at 150° C. in the HP7694 Headspace Sampler, which is commercially available from Agilent Technologies Inc. (Santa Clara, Calif.). Helium (1 mL heated at 160° C.) was used to extract an aliquot of the headspace gas and convey it via a transfer line heated at 180°

C. into the HP6890 Gas Chromatograph (GC) fitted with a ZEBRON ZB-5 ms column. This gas chromatograph is commercially available from Agilent Technologies Inc. (Santa Clara, Calif.). The column has dimensions of 30 meter by 0.32 millimeter by 1 micrometer and is commercially available from Phenomenex (Torrance, Calif.).

The GC column was heated from −20° C. to 150° C. at 10° C./min and from 150° C. to 310° C. at 20° C./min. The GC column was held at 310° C. for 5 minutes to ensure that the entire sample had been eluted. Helium was passed through the column with a flow rate of 2.0 mL/min. The separated components passed into the HP5973 mass selective detector where they were subjected to electron bombardment at 70 eV. The mass selective detector is commercially available from Agilent Technologies Inc. (Santa Clara, Calif.). A full scan unit resolution mass spectra from 29 to 500 m/z was detected and recorded.

X-Ray Scattering (XRD)

Samples were placed on zero background specimen holders composed of single crystal quartz. Reflection geometry data were collected in the form of a survey scan by use of a vertical diffractometer, copper $K_\alpha$ radiation, and proportional detector registry of the scattered radiation. The diffractometer, which is commercially available from PANalytical (Westborough, Mass.), was fitted with variable incident beam slits, fixed diffracted beam slits, and a graphite diffracted beam monochromator. The survey scan was conducted from 5 to 80 degrees (2θ) using a 0.04 degree step size and 24 second dwell time. The x-ray generator settings of 45 kV and 35 mA were used.

The observed diffraction peaks were subjected to profile fitting using a Pearson VII peak shape model, a cubic spline background correction model, and analysis using JADE version 7.5 X-ray diffraction software from MDI (Materials Data Inc. of Livermore Calif.). The apparent crystallite size (D) was determined using the Scherrer equation.

$$\text{Crystallite Size}(D) = K\lambda/\beta(\cos\theta)$$

In the Scherrer equation, K is the shape factor (here 0.9), λ is the wavelength of the x-ray radiation (here 1.540598 Å), β is the calculated peak width after correction for instrumental broadening (in radians), and θ equals half the peak position (scattering angle). β is equal to [calculated peak FWHM—instrumental breadth] (converted to radians) where FWHM is full width at half maximum.

The boehmite examples typically had a (020) peak that had a higher angle shoulder with the main peak and shoulder shifted to a lower and a higher angle relative to the expected position of the (020). Contrary to expectations based on the appearance of the (020), this splitting was not observed for the (080) peak. The (120) peak and the (031) peak with maxima at 28.2 and 38.3 degrees (2θ) respectively were used for evaluation of crystallite size.

Transmission Electron Microscopy

Samples for transmission electron microscopy were prepared on 400 mesh copper grids with a carbon/formvar coating from which the formvar had been removed via an acetone/chloroform/acetone wash. Approximately 1 microliter of the sample was dilusted to 3 mL with high resistance deionized water. The mixture was hand-shaken for several seconds to assure homogenization. One drop of the prepared mixture was placed upon its respective copper grid for about one minute to allow migration of the nanoparticles to the coated grid surface. The fluid was then wicked away at the edge of each grid with a tissue commercially available under the trade designation KIM WIPE. The grid plus nanoparticles were allowed to air dry for thirty minutes.

The transmission electron microscope was a Hitachi 9000, which is commercially available from Hitachi High Technologies Corporation (Tokyo, Japan), operating at 300 KeV acceleration potential. The instrument magnification was 20 KX. The nanoparticle images were collected using a Gatan ULTRASCAN 894 ccd camera (Gatan Inc. Pleasanton, Calif.) via DigitalMicrograph™ software. Calibration of the images is based upon TEM calibration standard MAG*I*CAL™ made by Norrox Scientific, Ontario, Canada. The images had a calibrated marker bar. Measurements were made by using DigitalMicrograph™ software and plug in "LabelLength" and then imported into Microsoft Excel (Microsoft Corporation Redmond, Wash.) to graph and calculate. Nanoparticle image domains were visually identified and particle shapes were manually described on each respective image. Frequent contact among nanoparticles and lack of contrast with image background precluded automatic image analysis. That is, the particles for analysis had to be manually identified for measurement. At least 100 particles were measured. The geometrical properties of the particles and the associated standard deviations were calculated.

Continuous Hydrothermal Reactor

The continuous hydrothermal reactor is shown schematically in FIG. 1. The feedstock was placed in a glass vessel positioned several feet higher than the inlet valve of the LEWA ECODOS diaphragm pump, which is commercially available from LEWA GmbH (Stuttgart, Germany). The glass vessel had a stock cock that could be opened to allow the feedstock to exit the glass vessel. Polyethylene tubing connected the glass vessel to the inlet of the diaphragm pump. The reactor portion was 50 feet of 0.25 inch ID Teflon hose with a braided stainless steel exterior which is immersed in an electrically heated peanut oil bath. The Teflon hose was obtained from Saint-Gobain Performance Plastics (Bridgewater, N.J.). The product of the reactor was then cooled by flowing through 10 feet of 0.25" OD stainless steel tubing in an ice water bath. The backpressure for the system is provided by a backpressure regulator, which is commercially available from Tescom (Elk River, Minn.). Another piece of polyethylene tubing was used to transport the product to a suitable collection vessel. The reactant flow rate was checked periodically using a graduated cylinder and a stopwatch. The flow was adjusted by changing the length of the pump stroke. The peanut oil temperature was measured using a thermocouple which provided feedback to a computer control algorithm for the autoclave heating elements. The peanut oil was stirred by a propeller mixer powered by an air motor.

Preparatory Examples 1 to 5

Aluminum-containing precursors were prepared by digesting powdered aluminum in a mixture of various carboxylic acid mixtures and water. The spherical aluminum powder was purchased from Aldrich, Milwaukee, Wis. Glacial acetic acid (99.5% acid) was purchased from EMD Chemicals, Darmstadt, Germany, formic acid (97% acid) was purchased from Alfa Aesar, Ward Hill, Mass., and propionic acid (99%) was purchased from Avocado Research Chemicals Ltd, Shore Road, Heysham, Lancashire, UK.

The compositions of the digestion mixtures are summarized in Table 1.

TABLE 1

Preparation of the Aluminum-containing precursor

| Preparatory Example | Aluminum Powder (g) | Formic Acid (g) | Acetic Acid (g) | Propionic Acid (g) | Water (g) | Total Weight (g) |
|---|---|---|---|---|---|---|
| 1 | 27.0 | 19.0 | 48.2 | 0.0 | 405.8 | 500 |
| 2 | 27.0 | 28.5 | 36.2 | 0.0 | 408.3 | 500 |
| 3 | 27.0 | 38.0 | 24.2 | 0.0 | 410.9 | 500 |
| 4 | 27.0 | 47.4 | 12.2 | 0.0 | 413.5 | 500 |
| 5 | 27.0 | 28.5 | 0.0 | 44.8 | 399.7 | 500 |

The components of each digestion mixture were combined in a 1000 ml round bottom flask equipped with a reflux condenser, a magnetic stirrer, and a heating mantle. After heating each mixture was heated to about 80° C., an exothermic reaction commenced. The heat released from the reaction increased the temperature above 80° C. but below 100° C. After about an hour, the temperature was about 80° C. At this point the temperature set point for the heating mantle was raised to about 100° C. The temperature remained at 100° C. for 10 to 16 hours or until no more hydrogen gas was observed escaping from the reactor vent glycerin trap. The heating mantle was turned off and the solution was allowed to cool to room temperature. The solution was then vacuum filtered through a first filter (Whatman Filter No. 50 from Whatman International Ltd., Maidstone, England) and then filtered through a second filter (Whatman Filter No. 54 from Whatman International Ltd.). The resulting product had an aluminum content of about 5.4 weight percent based aluminum based on the weight of the total digestion mixture.

Examples 1 to 6

Preparatory Examples 1 to 5 were each diluted with 500 mL deionized water and then passed through the continuous hydrothermal reactor. The temperature of the reactor portion was controlled at 170° C. The flow rates used were either 10 mL/minute for a 48 minute residence time or 20 mL/minute for a 24 minute residence time within the heated reactor portion.

Most of the examples (Examples 1, 2, 4, 5, 6) were dried at 70° C. in a horizontal air flow batch oven. The effluent from the continuous hydrothermal reactor for each example was poured into PYREX pans (Corning Inc. Life Sciences, Lowell, Mass.) to a depth of approximately 6 millimeters. The pan was placed into the oven where it remained overnight. The dried material was a translucent brittle film that was easily removed with a stainless steel laboratory spatula from the glass pan and placed into a clean glass jar.

Example 3 was dialyzed. The effluent from the continuous hydrothermal reactor was poured into a SPECTRAPOR membrane, which is commercially available from Spectrum Labs (Rancho Dominguez, Calif.), with a 6 to 8000 molecular weight cut off. The membrane was closed at the bottom with an overhand knot. The top of the membrane was subsequently tied off with an overhand knot and the tube of material was placed in a one gallon jar filled with deionized water. The water in the jar was changed every working day for two weeks. A sample of this material was dried for subsequent testing in the same manner as the rest of the samples as detailed above.

TABLE 2

Preparation of Acicular boehmite nanoparticle

| Example | Preparatory Example | Flow rate (mL/min) | Post-treatment |
|---|---|---|---|
| 1 | 1 | 10 | Dried |
| 2 | 2 | 20 | Dried |
| 3 | 2 | 10 | Dialysis, then dried |
| 4 | 3 | 10 | Dried |
| 5 | 4 | 10 | Dried |
| 6 | 5 | 10 | Dried |

Figure 2:
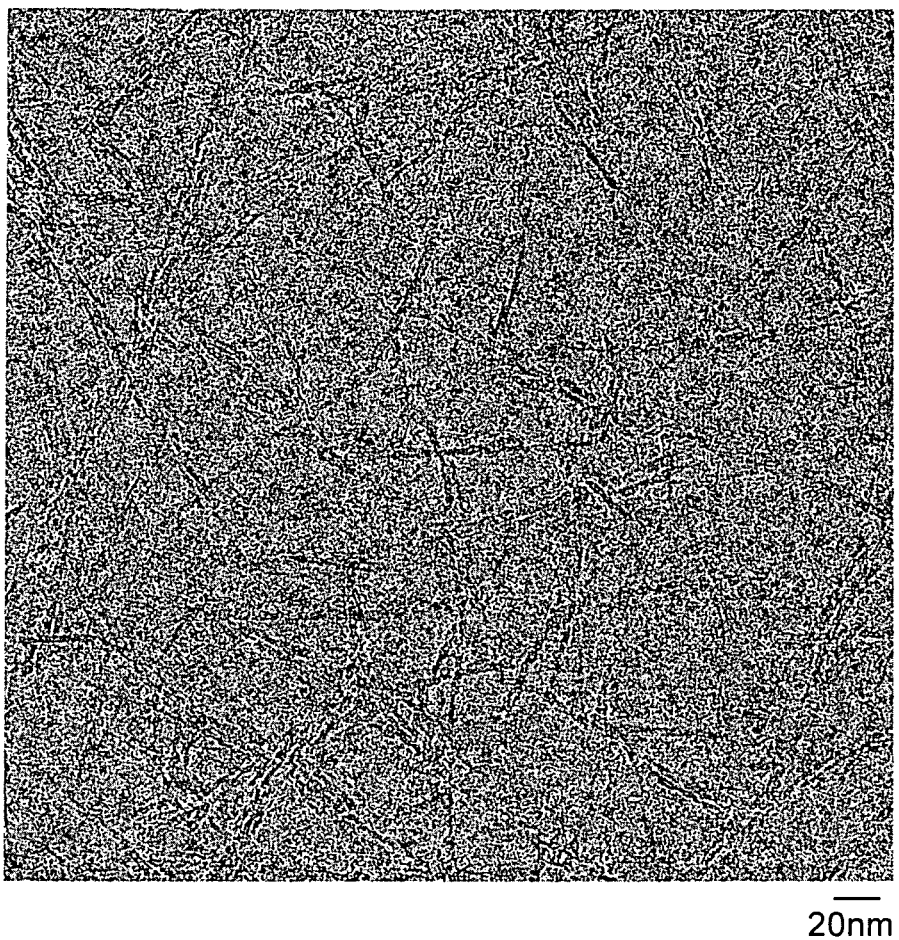
FIG. 2 shows an exemplary transmission electron micrograph of the acicular boehmite nanoparticle.

Table 3 summarizes the results from the thermogravimetric analysis (TGA), x-ray diffraction (XRD), and transmission electron microscopy (TEM) for Example 1 to 6. The TGA Weight Loss, which corresponds to the temperature where any residual carboxylic acid might be removed, is equal to the percentage of the initial weight lost between 47° C. and 111° C. The Crystallite Size is determined using XRD. Average particle length, average particle width, and aspect ratio were determined by measurement of at least 50 particles from a transmission electron micrograph of each example; the results are summarized in Table 4. Table 5 summarizes the gas chromatographic/mass spectroscopic (GC/MS) headspace analysis of Examples 1 to 6. FIG. 2 is the transmission electron micrograph for Example 6.

TABLE 3

TGA and XRD of Examples 1 to 6

| Example | TGA Weight Loss (%) | TGA Residue (%) | XRD Crystallite Size (nm) |
|---|---|---|---|
| 1 | 9.60 | 71.00 | 4.7 |
| 2 | 5.24 | 72.06 | 3.1 |
| 3 | 4.64 | 72.48 | 3.4 |
| 4 | 4.60 | 70.80 | 3.3 |
| 5 | 11.90 | 63.90 | 3.5 |
| 6 | 6.94 | 68.05 | 3.9 |

TABLE 4

TEM Analysis of Examples 1 to 6

| Example | Major Axis (nm) | Standard Deviation (nm) | Minor Axis (nm) | Standard Deviation (nm) | Aspect Ratio | Standard Deviation |
|---|---|---|---|---|---|---|
| 1 | 74.1 | 33.3 | 7.7 | 2.5 | 10.2 | 4.8 |
| 2 | 58.9 | 28.9 | 8.4 | 3.4 | 7.9 | 4 |
| 3 | 76.6 | 23.7 | 14.7 | 3.7 | 5.4 | 1.6 |
| 4 | 73.7 | 22.7 | 15.5 | 3.2 | 4.9 | 1.4 |
| 5 | 73.5 | 37.0 | 5.7 | 1.9 | 14.0 | 8.2 |
| 6 | 88.5 | 39.0 | 4.2 | 1.6 | 22.4 | 11.2 |

TABLE 5

Headspace Analysis of Examples 1 to 6

| Example | Water (% area) | Formic acid (% area) | Acetic acid (% area) | Propionic acid (% area) |
|---|---|---|---|---|
| 1 | 79.90 | 10.98 | 9.08 | |
| 2 | 66.54 | 18.97 | 12.89 | |
| 3 | 99.63 | 0.29 | 0.08 | |
| 4 | 72.44 | 13.62 | 13.70 | |
| 5 | 58.58 | 26.33 | 13.90 | |
| 6 | 49.08 | 35.34 | 0.92 | 14.26 |

Example 7

The acicular boehmite can be modified to facilitate use in an organic matrix. The dried acicular boehmite nanoparticle of Example 2 (1.75 grams) can be dispersed in deionized water (48.25 grams) at room temperature in one hour by mixing with a magnetic stirrer. With continued stirring, 1-methoxy-2-propanol (92.4 grams) from Alfa Aesar (Ward Hill, Mass.) can be added to the mixture. Then, 3-trimethoxysilylpropylmethacrylate (1.3 grams) from Alfa Aesar can be added to the mixture. This mixture can be heated in a water bath with magnetic stirring at 80° C. for four hours. After this, the mixture can be stripped under vacuum using a rotary evaporator (Büchi Labortechnik AG, Flawil, Switzerland) until the concentration becomes thick. The percent solids is often about 18 weight percent. Then, trimethylolpropane triacrylate (27 grams) from Alfa Aesar can be added. The mixture can then be stripped under vacuum for three days at 80° C. in the rotary evaporator to remove 1-methoxy-2-propanol from the mixture. The final mixture appears more viscous than the neat trimethylolpropane triacrylate.

Example 8

The aluminum-containing precursor for Example 8 was prepared by digesting 27 grams of aluminum powder (Aldrich Chemical Company, Milwaukee, Wis.) in a solution containing a mixture of 30.2 grams of glacial acetic acid (EMD Chemicals, Darmstadt, Germany), 23.7 grams of formic acid (Alfa Aesar, Ward Hill, Mass.), 17.8 grams of methoxy-ethoxy-ethoxy-acetic acid (MEEAA, Aldrich Chemical Company, Milwaukee, Wis.), and 401.3 grams of deionized water using the same process as described in the previous examples. The resulting solution was then vacuum filtered in the same manner as previously described. The filtered solution was then diluted with an additional 500 grams of deionized water. This precursor solution was then passed through the continuous hydrothermal reactor at a flow rate of 10 ml per minute for a mean residence time of 48 minutes. The product material was later analyzed using transmission electron microscopy. The particle size analysis is shown in Table 6.

Example 9

The aluminum-containing precursor for Example 9 was similar to the precursor that was described in Preparatory Example 2 except that lactic acid solution (about 9 grams or 0.1 mole, Aldrich Chemical Company, Milwaukee, Wis.) was added to the product of the digestion reaction. This solution was subsequently diluted with an additional 500 grams of deionized water and then passed as the feedstock through the continuous hydrothermal reactor at a flow rate of 10 ml per minute for a mean residence time of 48 minutes. The product material was later analyzed using transmission electron microscopy. The particle size analysis is shown in Table 6.

We claim:

1. A method of making an acicular boehmite nanoparticle, the method comprising:
   providing a feedstock solution comprising an aluminum-containing precursor dissolved in an aqueous-based solvent at a pH no greater than 6, the aluminum-containing precursor being of Formula (I)

$$Al(OH)_w(R^1)_x(R^2)_y(R^3)_z \qquad (I)$$

wherein
   $R^1$ is a first carboxylate selected from a formate or acetate;
   $R^2$ is a second carboxylate that is different from the first carboxylate and that is selected from acetate, propionate, butyrate, or mixtures thereof;
   $R^3$ is an optional third mono-carboxylate having at least 5 carbon atoms;

$$w+x+y+z=3;$$

w is in a range of 1.5 to 2.2;
   x is equal to at least 0.1;
   y is equal to at least 0.1; and
   z is in a range of 0 to 0.2; and
   passing the feedstock solution through a continuous hydrothermal reactor held at a temperature in a range of 150° C. to 180° C., wherein an effluent of the continuous hydrothermal reactor comprises the acicular boehmite nanoparticle.

2. The method of claim 1, wherein
   the acicular boehmite nanoparticle has an average length no greater than 500 nanometers and an average width no greater than 15 nanometers.

3. The method of claim 1, wherein $R^1$ is formate and $R^2$ is acetate, propionate, or a mixture thereof.

4. The method of claim 1, wherein x is in the range of 0.5 to 1.3 and y is in the range of 0.2 to 1.0.

5. The method of claim 1, wherein the feedstock solution contains the aluminum-containing precursor in an amount in a range of 0.1 to 5 molar.

6. The method of claim 1, wherein the effluent further comprises (a) a dissolved first carboxylic acid, a dissolved anion of the first carboxylic acid, or a mixture thereof wherein the first carboxylic acid is selected from formic acid or acetic acid, and (b) a dissolved second carboxylic acid, a dissolved anion of the second carboxylic acid, or a mixture thereof wherein the second carboxylic acid is different than the first carboxylic acid and is selected from acetic acid, propionic acid, butyric acid, or a mixture thereof.

7. The method of claim 6, further comprising removing at least a portion of (a) the dissolved first carboxylic acid, the dissolved anion of the first carboxylic acid, or a mixture thereof, and at least a portion of (b) the dissolved second carboxylic acid, the dissolved anion of the second carboxylic acid, or a mixture thereof.

8. The method of claim 1, further comprising adding a surface modifying agent to a surface of the acicular boehmite nanoparticle.

TABLE 6

| | TEM Analysis of Examples 8 and 9 | | | | | | | | |
|---|---|---|---|---|---|---|---|---|---|
| Ex. | Ave. Length (nm) | Median Length (nm) | Stand. Dev. (nm) | Ave. Width (nm) | Median Width (nm) | Stand. Dev. (nm) | Ave. Aspect Ratio | Median Aspect Ratio | Stand. Dev. |
| 8 | 109.5 | 95.9 | 12.4 | 4.9 | 4.9 | 1.8 | 23.4 | 20.6 | 12.4 |
| 9 | 148.2 | 136.7 | 76.3 | 13.9 | 13.7 | 7.1 | 11.9 | 10.9 | 6.6 |

9. The method of claim 1, further comprising removing at least a portion of an aqueous-based solvent from the effluent.

10. The method of claim 1, further comprising dispersing or suspending the acicular boehmite nanoparticle in an organic matrix.

11. The method of claim 1, wherein the feedstock solution further comprises (a) a mono-carboxylic acid having a polyalkylene oxide group or (b) an alpha-hydroxyl carboxylic acid having a single carboxyl group.

12. The method of claim 1, wherein the continuous hydrothermal reactor comprises a heated tubular reactor.

13. The method of claim 12, wherein an interior of the tubular reactor is lined with a fluorinated polymeric material.

14. The method of claim 13, wherein the polymeric material comprises a fluorinated polyolefin.

15. The method of claim 1, wherein $R^3$ is mono-carboxylate comprising a poly(alkylene oxide) group.

* * * * *

UNITED STATES PATENT AND TRADEMARK OFFICE
CERTIFICATE OF CORRECTION

PATENT NO. : 9,102,690 B2
APPLICATION NO. : 12/810041
DATED : August 11, 2015
INVENTOR(S) : Grant Tiefenbruck It is certified that error appears in the above-identified patent and that said Letters Patent is hereby corrected as shown below:

Title Page, Item (87), Column 1 (PCT Pub. Date)
Line 1, delete "Nov. 9, 2009" and insert -- Sep. 11, 2009 --, therefor.

In the Specification

Column 12
Line 21, delete "N-methylpyrrolidone." and insert -- N-methyl pyrrolidone. --, therefor.

Signed and Sealed this
Twenty-eighth Day of June, 2016

Michelle K. Lee
*Director of the United States Patent and Trademark Office*